United States Patent [19]
Yamashita

[11] Patent Number: 6,125,856
[45] Date of Patent: Oct. 3, 2000

[54] HAIR REPAIR, STYLING, AND STRAIGHTENING PROCESS

[75] Inventor: Yuko Yamashita, Tokyo, Japan

[73] Assignee: Phild Co., Ltd., Kyoto, Japan

[21] Appl. No.: 09/296,689

[22] Filed: Apr. 21, 1999

[51] Int. Cl.[7] .............................. A45D 24/00; A45D 7/04; A61K 7/06; A61K 7/09

[52] U.S. Cl. ..................... 132/204; 132/200; 132/205; 424/70; 424/71; 424/70.2; 424/72

[58] Field of Search ................... 132/200, 202, 132/204, 205, 206, 211, 221, 270; 424/70.2, 70.1, 72, 70, 71

[56] References Cited

U.S. PATENT DOCUMENTS

| | | | |
|---|---|---|---|
| 4,361,157 | 11/1982 | James ............................................. | 132/7 |
| 4,592,908 | 6/1986 | Wajaroff et al. ............................. | 424/71 |
| 4,602,648 | 7/1986 | Syed et al. .................................... | 132/7 |
| 4,659,566 | 4/1987 | Petrow ......................................... | 424/71 |
| 5,060,680 | 10/1991 | Akhtar ........................................ | 132/204 |
| 5,294,230 | 3/1994 | Wu et al. ..................................... | 424/72 |
| 5,476,650 | 12/1995 | Patel ........................................... | 424/70.2 |
| 5,562,110 | 10/1996 | Ottenbrite et al. ........................ | 132/202 |
| 5,609,859 | 3/1997 | Cowsar ...................................... | 424/70.4 |
| 5,679,327 | 10/1997 | Darkwa et al. ............................ | 424/70.4 |

*Primary Examiner*—John J. Wilson
*Assistant Examiner*—Robyn K. Doan
*Attorney, Agent, or Firm*—James E. Curry

[57] ABSTRACT

An improved hair repair, styling, and straightening process wherein the optimal reaction point of the hair with the straightening solution is more accurately controlled and monitored. The hair straightening solution has a unique jell-like consistency to more completely and easily be rinsed from the hair. A unique pre-oxidizing set is applied to the hair by application of heat and compression while the hair remains in an elastic condition. The pre-oxidizing set provides the ability to make fine styling adjustments to the hair. A substantial improvement in straightening, styling, and repairing damaged hair is achieved.

11 Claims, No Drawings

HAIR REPAIR, STYLING, AND STRAIGHTENING PROCESS

BACKGROUND OF THE INVENTION

1. Field of the Invention

The invention relates in general to hair straightening processes and, in particular, to an improved hair repair, styling, and straightening process wherein the optimal reaction point of the hair with the hair straightening solution is more accurately controlled and monitored. The hair straightening solution has a unique jell-like consistency to more completely and easily be rinsed from the hair. A unique pre-oxidizing set is applied to the hair by application of heat and compression while the hair remains in an elastic condition due to reaction with the hair straightening solution. The pre-oxidizing set also provides the ability to make fine styling adjustments to the hair. The result of the process is a substantial improvement to the hair's sheen and surface structure compared to other prior art hair straightening methods.

2. Description of the Prior Art

Highly alkaline, permanent hair straightening solutions are well known in the hair care art. When applied to hair, these highly alkaline solutions alter the molecular bonds of the protein, molecules that make up the hair. While in this altered state, the hair is mechanically straightened by the application of tension forces, typically by combing, and/or styled on rollers. In addition, protein conditioners are often introduced so as to bond with the hair to repair damage such as frizzles, split ends, and the like. The introduced protein is intended to improve the feel and sheen of the hair. The hair is then allowed to oxidize and return to its molecularly unaltered state. Most often, an acidic neutralizer solution is applied to expedite the oxidation process.

Such hair straightening processes utilizing these strong chemicals are somewhat hazardous and can cause damage to the hair. The highly alkaline solutions are an irritant to the scalp and, when in contact with the scalp, can result in hair loss when the hair is mechanically straightened by combing. Often times the alkaline solutions are provided in a a generally rigid cream or paste form so their application to the scalp can be avoided. However these creams or pastes are difficult to rinse out. Sometimes oleaginous materials are added to the solutions in an oil-in-water emulsion in order to protect the scalp. These solutions are also difficult to rinse out. When the residue of the alkaline solution remains in the hair, the ability to improve the quality of the hair structure by conditioning is reduced. Thus, there is a need to provide an alkaline hair straightening solution that can be more easily and completely rinsed out of the hair in order to increase protein bonding and further improve the feel and sheen of the hair.

Determining the amount of time the alkaline solution must remain in the hair has proven problematic. Many factors influence the amount of time necessary for the alkaline solution to optimally react with the hair. Some of these factors are: the thickness of the hair fibers, the ph strength of the solution, the temperature of the hair and solution combination, and the moisture content. It has been discovered that the temperature during treatment is not uniform and, undesirably, certain portions of the hair will react to the solution at different rates than other portions. This non-uniform reaction is further complicated because some portions of the hair can dry out faster than other portions, and this also alters the rates of reaction of the solution to the various portions. Mechanically straightening the hair prematurely can damage the hair, can cause the hair to break, or can simply produce a poor quality hair straightening treatment. Likewise, it is well known that allowing the alkaline solution to remain on the hair too long can also damage the hair. Monitoring and/or controlling these factors is critical in obtaining optimal and consistent results, however, a reliable and consistent procedure to monitor and/or control these factors is not found in the prior art. For instance, determining when the hair has been sufficiently subjected to the hair straightening solution has been imprecise in the art since the determination is often left to the subjective opinion of the stylist. Thus, there is a need to more precisely and uniformly monitor and control the reaction rate and optimal reaction point of the alkaline solution with the hair.

Often, protein conditioners are introduced to the hair during the hair straightening process. It is desirous that these proteins bond to the hair structure and thereby improve the surface of the hair. Microscopically, a hair strand grows in overlapping flap layers. Being able to more completely rinse the alkaline hair straightening solution and its residue from the hair, particularly between the flap layers of the hair, increases the ability for the protein conditioners to penetrate and bond the flap layers. Increased protein conditioner bonding of these flap layers substantially improves the feel and sheen of the hair. Thus, there is a need to improve the feel and sheen of the hair by increasing protein conditioner penetration of the hair to bond the flap layers of the hair during the hair straightening process.

These and other difficulties of the prior art have been overcome according to the present invention. Those concerned with these problems recognize the need for an improved hair repair, straightening, and styling process.

BRIEF SUMMARY OF THE INVENTION

The present invention provides its benefits across a broad spectrum of hair repair, styling and straightening processes. While the description which follows hereinafter is meant to be representative of a number of such applications, it is not exhaustive. As those skilled in the art will recognize, the basic methods taught herein can be readily adapted to many uses. It is applicant's intent that this specification and the claims appended hereto be accorded a breadth in keeping with the scope and spirit of the invention being disclosed despite what might appear to be limiting language imposed by the requirements of referring to the specific examples disclosed.

It is one object of the present invention to provide an improved method for permanently straightening, repairing, and styling hair.

It is another object of the present invention to provide an alkaline hair straightening solution that can be more easily and more completely rinsed out of the hair.

It is another object of the invention to more precisely and more uniformly control the reaction rate of the hair to the alkaline hair straightening solution.

It is another object of the invention to consistently, accurately, and repeatedly determine when the optimal point of reaction between the hair and the alkaline hair straightening solution has occurred.

It is still another object of the invention to provide the ability to make fine styling adjustments to the hair during the straightening process.

It is still another object of the invention to provide an improved hair straightening process wherein the structural condition of each hair is significantly improved over prior art hair straightening processes.

A preferred embodiment of the hair repair and straightening process according to the present invention comprises the steps of washing and rinsing the hair and then applying an alkaline hair straightening solution. A thioglycolic alkaline solution having a jell-like consistency is preferred. As used herein, a solution having a jell-like consistency is a solution being a thixotropic jell, that is one that when at rest can resist shear stresses and stand, but when shaken is unable to resist shear stresses and moves as a liquid. Initially the solution is not applied in the nape area of the head, that is, the lower two inch portion of hair just above the back of the neck running from ear to ear. To more precisely and uniformly control the reaction rate of the hair to the solution, the hair is then wrapped in a plastic covering. Uniquely, the optimal point where the hair has reacted to solution is initially determined by an elastic stretch test of approximately five or so hair strands. When these strands elastically stretch approximately between about 25 to 50 percent, the time is noted and the optimal point is near. The solution is then applied to the portion of hair in the nape section, the plastic wrap is again placed over the hair, and the solution is allowed to remain on the hair for approximately half the time noted above. At this point the optimal point of reaction with the solution is complete. The hair is then suspended in this state by rinsing out the alkaline solution. Importantly, due to the jell-like consistency of the alkaline solution, the solution can be more completely and more easily rinsed from the hair as compared to other prior art alkaline hair straightening creams or pastes. The ability to more thoroughly rinse out the alkaline solution advantageously and effectively prepares the hair for improved protein penetration and bonding. Once all residue of the alkaline solution has been removed by rinsing, a hair repairing solution is applied to the hair. The hair repairing solution introduces protein molecules for penetrating and bonding to the hair. Uniquely, a pre-oxidizing set is then applied to the hair by compressing the hair under heat. The pre-oxidizing set significantly improves the bonding of the protein molecules to the surface of the hair, and more particularly improves the bonding of the overlapping flap layers of the individual hair strands. The pre-oxidizing set, due to the application of compression and heat, temporarily structurally sets the hair and allows the straightened hair to be precisely styled into various configurations, such as, gentile waves, and the like. This allows for very sensitive styling adjustments to be made to the hair which has not been previously obtainable by the use of curlers or rollers, and the like. Preferably, a flat hair iron operated between about 180 and 130 degrees Celsius is used to apply the compression and heat to the hair, with less heat applied to more damaged hair. Carefully, the entire length of every hair is compressed under heat by the iron. Uniquely, it has been found that compressing the hair under heat produces significantly improved hair straightening and repairing results compared to the application of tensile forces of the prior art. The hair is then allowed to cool down to ambient temperature, and an acid rinse is applied in preparation of applying a neutralizer solution. The neutralizer solution is then applied which oxidizes the hair and eliminates the elastic condition of the hair caused by the alkaline hair straightening solution. The hair is then rinsed to remove the neutralizer solution and is then dried. A second application of compression and heat may be applied, if desired.

It has been found that, when the degree of damage present in the hair increases, it is desirable to include oil, such as matricaria oil, in small amounts to the hair repairing solution or conditioner. It is believed the oil helps prevent the hair from undesirably losing too much moisture before being neutralized, and has produced improved results in the treatment of heavily damaged hair.

What is achieved is an improved hair straightening, repairing, and styling process. The feel and sheen of the hair is significantly improved. Frizzled hair, typically found even in generally straight hair, is restructured straight and their surfaces are repaired. Very precise styling adjustments can also be obtained. The process takes approximately three to four hours, but the effects of the process can last up to about six months.

Unexpectedly, it has been discovered the benefits of this process provide a significant improvement over other prior art hair straightening methods.

Other objects, advantages, and novel features of the present invention will become apparent from the following detailed description of the invention.

DETAILED DESCRIPTION OF THE PREFERRED EMBODIMENTS

The hair straightening, repairing, and styling process of the present invention starts with an initial washing and rinsing of the hair. The main purpose of washing the hair is to get rid of the impurities discharged in the scalp, not necessarily to clean the impurities in the hair. Thus, when washing the hair, gentle massaging of the hair is to be directed on the scalp area in order to assure the impurities in the scalp are discharged. Any appropriate hair cleansing shampoo can be used, although it is preferable the shampoo does not contain perfumes or other ingredients intended to remain in the hair after rinsing. If the hair is extremely dirty, the shampoo, after being gently massaged into the hair, should be allowed to remain in the hair at least one minute before rinsing. After a thorough rinsing of the hair in water, the hair is then towel dried to remove the excess moisture. It has been found desirable to remove approximately 50% of the water moisture from the hair.

Depending on the condition of the hair, as more particularly discussed in the examples below, a protein conditioner may be introduced to the hair prior to application of the alkaline hair straightening solution. Uniquely, the alkaline hair straightening solution of the present invention has a jell-like consistency. A thioglycolic alkaline solution with an appropriate amount of hydroxyethylcellulose and water provides the appropriate jell-like consistency required, that is, one that when at rest can resist shear stresses and stand, but when shaken is unable to resist shear stresses and moves as a liquid. The solution is applied in layers to the hair with special care made to avoid application to the scalp or roots of the hair. The jell-like consistency of the solution, just as the prior art cream or paste formulations, assists in preventing the solution from undesirably migrating to the scalp. Alkaline solutions having a liquid consistency are undesirable because, when applied, they will migrate into the scalp causing both skin irritation and damage to the hair cuticles. The jell-like consistency of the solution of the present invention advantageously makes it substantially easier to completely rinse the solution from the hair as compared to the prior art creams and pastes, yet can still be applied to avoid contact with the scalp.

Initially, the solution is not applied to the hair in the nape area of the head, that is, the lower two inch portion of the hair just above the back of the neck running from ear to ear. This is because this portion of the head radiates a significant amount of heat due to blood flow to the brain. This heat raises the temperature of the hair in this area, and if the solution is initially applied to the hair in the nape area it would chemically react to the solution much faster than the rest of the hair. This is undesirable and would produce non-uniform results, and can even cause damage to the hair in the nape area.

When applying the alkaline hair straightening solution to the hair, it is extremely important to avoid contact of the solution with the scalp. This is accomplished with the following procedure. The hair is parted into blocks and the alkaline hair straightening solution is applied individually to each block. Treatment of the blocks is started with the blocks at the bottom of the head above the nape area and continued while working up to the top of the head. Each block is gently lifted outward from the head, and the solution is applied to the hair starting about 2 centimeters away from the scalp. After a block has been treated it is carefully laid down and the next block is treated, and so on, until all the hair, with the exception of that portion in the nape area, is treated. This procedure assists to minimize the undesirable problems that occur when the solution gets into direct contact with the scalp. The jell-like consistency of the solution avoids this problem by preventing the solution from migrating to the scalp, as would occur is the solution had a liquid consistency. Thus, the jell-like consistency of the solution is an optimal compromise in providing the easiest solution to be thoroughly rinsed from the hair while also preventing the solution from migrating to the scalp.

Once the solution has been carefully applied in layers or blocks to the hair, as discussed above, the hair is covered with a clear plastic wrap. Uniquely, the plastic wrap functions to more evenly regulate the temperature of the hair as it reacts to the alkaline solution, and simultaneously prevents the hair from drying out. Thus, the plastic wrap functions to more precisely and more uniformly control the reaction rate of the hair to the alkaline solution. This improves the results achieved by the hair straightening and repairing process.

Between about four to twenty minutes, depending on the condition of the hair as discussed in the six examples below, the solution remains in the hair under the plastic wrap until the elastic stretch test is conducted. Uniquely, the elastic stretch test allows the stylist to more consistently, accurately, and repeatedly determine when the optimal point of the reaction between the hair and the alkaline hair straightening solution has occurred. It has been discovered that the optimal point occurs when the hair transitions into a highly elastic condition. Approximately about five or so hair strands are grasped approximately about three centimeters apart and are pulled. When these strands are able to elastically stretch to approximately about four to four and a half centimeters and return back to about three centimeters, that is, elastically stretch approximately between about 25 to 50 percent, the optimal point is near. When the test is satisfied the time the solution has remained in the hair is noted. The alkaline solution is then applied to the portion of hair in the nape area, and the plastic wrap is again placed over the hair. The solution is then allowed to remain on the hair one half the time previously noted, at which time the optimal point has been reached.

The hair is suspended in its elastic condition by rinsing out the alkaline solution. As a result of the unique jell-like consistency of the solution, the solution is more easily and completely rinsed from the hair as compared to other prior art alkaline hair straightening creams or pastes. Preferably the rinse is accomplished with lukewarm water under low water pressure while gently massaging the hair. Care must be taken in handling the hair while rinsing to avoid breaking or pulling out hair. The hair may also be shampooed and rinsed at this step, if desired. The hair is then towel dried.

A hair repairing solution or conditioner is then applied to the hair containing protein molecules. These molecules improve the feel and sheen of the hair when they bond to the hair. Proteins such as, for example, Collagen, Keratin, Elastin, and combinations thereof, may be used, as desired. After application of the hair repairing solution, a substantial amount of moisture is removed from the hair. This is accomplished by combing and blow drying. Ideally, approximately about 70 percent of the total moisture in the hair should be removed, but the amount removed should not exceed 80 percent. If too much moisture is removed, the hair must be sprayed with purified water and then again combed and blow dried.

A pre-oxidizing set is applied to the hair by physically compressing substantially the entire length of each hair strand under heat. The pre-oxidizing set is unique in that the compressive forces and the heat, in the presence of the protein molecules, substantially improve the surface structure of the hair. The compression and heat substantially eliminates the natural overlapping flap layers of the hair due to the bonding action of the protein molecules. This can not be accomplished as effectively under the prior art hair straightening methods that apply tension forces to the hair by combing. Preferably, a flat hair iron is used to apply the compression and heat to the hair. The hair is compressively ironed in small bundles of strands, preferably the bundles of strands being approximately about ¾ of a centimeter in diameter. Ironing is started about two centimeters from the scalp working outward to the hair ends. The compression of the iron is cyclically applied in an overlapping manner across the entire length of the bundle of strands. A new bundle of strands is then selected and the ironing repeated until all the hair has been ironed. The ironing of the pre-oxidizing step generally takes between about a half hour to about an hour and a half, depending on the length of the hair.

The pre-oxidizing set, due to the application of compression and heat, temporarily structurally stabilizes the hair and allows the straightened hair to be precisely styled into various configurations, such as, gentile waves and the like, if desired. Because the hair is uniquely structurally stabilized, very sensitive styling adjustments can be made to the hair, adjustments which have been previously unobtainable by the use of curlers or rollers, and the like. For example, a gentle curl can be made simply and precisely by slightly bending the hair when applying the iron cyclically down its length during the pre-oxidation set step.

The hair is then allowed to cool to ambient temperature, and an acid rinse is applied in preparation of applying a neutralizer solution. It is desired to lower the ph level of the hair to approximately 5.5 with the acid rinse, in order to eliminate all residue of the alkaline hair straightening solution. The acid rinse, if desired, can be selected from either citric acid, malic acid, oleic acid, sorbic acid, phosphate acid, or combinations thereof, as is well known in the art. Preferably the acid rinse is delivered to the hair via a pump spray.

The neutralizer solution is then applied to the hair in the same manner as the alkaline hair straightening solution was applied, with special care to avoid application of the solution to the scalp and roots of the hair. The neutralizer solution oxidizes the hair and eliminates the elastic condition of the hair resulting from its reaction with the alkaline hair straightening solution. It has been found that a neutralizer solution containing sodium bromate as the active ingredient works well in eliminating the elastic condition of the hair. The neutralizer solution need only remain on the hair for about ten minutes in order to eliminate the elastic condition of the hair. The hair is then rinsed with lukewarm water to remove the neutralizer solution and is then dried. A second application of compression and heat may be applied, if desired.

The following non-limiting examples illustrate the improved hair repair, styling, and straightening process of the present invention for use with various conditions of both thin and thick hair.

EXAMPLE 1

This example is intended for use on generally undamaged thin hair. Such hair, for example, would have very little, if any, split ends or frizzles, and may already be in a generally straight condition. Typically such hair has not been previously permed or colored The hair is first washed and rinsed with a shampoo, as previously discussed, in order to remove contaminants from the hair and scalp so that protein conditioners can more effectively penetrate and bond to the hair during the process. After rinsing, the hair is towel dried to remove excess moisture.

The alkaline base hair straightening solution is then applied, as more particularly discussed above, to the hair. Care must be taken to avoid contact of the solution with the root of the hair and the scalp of the head. Once applied, it is preferred to place a plastic wrap, as more particularly discussed above, over the hair to maintain a more even temperature of the hair so that the chemical reaction of the solution with the hair is evenly distributed. Between about 20 to 18 minutes the hair is stretch tested, as discussed above, to determine when the hair has transitioned into the structurally elastic condition. Once it has been determined that the hair has transitioned into the structurally elastic condition, the time is noted, the alkaline solution is then applied to the portion of hair in the nape area, the plastic wrap placed over the hair, and the solution is allowed to remain on the hair about half the time noted. At this point, the optimal point of reaction of the hair to the alkaline solution is achieved, and the hair is then suspended in this condition by rinsing with lukewarm water under low water pressure. Preferably the hair is then shampooed and rinsed to insure all of the residue of alkaline base hair straightening solution has been removed. After the rinse, the hair is then towel dried.

While the hair remains in the structurally elastic condition, a hair repairing solution or protein conditioner is applied to the hair via spray. Preferably, the hair repairing solution is a liquid protein conditioner containing the proteins Elastin, Keratin, and Collagen. It has been found that the combination of proteins of Hydrolized Collagen, Hydrolized Elastin, and Hydrolized Keratin work well in a hair repairing solution for treating thin hair. As one skilled in the art realizes, many other protein combinations can be used to produce an effective protein conditioner for thin hair. Once the hair repairing solution has been applied, a substantial amount of moisture is removed from the hair. This is accomplished by combing and blow drying. Ideally, approximately about 70 percent of the total moisture in the hair should be removed, but the amount removed should not exceed 80 percent. If too much moisture is removed, the hair must be sprayed with purified water and then again combed and blow dried.

The pre-oxidizing set is then applied to the hair. The pre-oxidizing set is accomplished by compressing the hair while subjecting it to heat, as discussed previously. In this example a flat hair iron is used at a temperature of 180 degrees Celsius. The combination of compression and heat work to stabilize the hair into a straight configuration, to significantly enhance bonding of the proteins from the hair repairing solution to the hair, and to partially neutralize the structurally elastic condition of the hair. Once the hair has been pressed it is allowed to cool off to ambient temperature. To speed up the cooling of the hair, a hair dryer may be used, as desired.

It is to be appreciated that the pre-oxidizing set acts to temporarily set the hair, which allows the hair to be advantageously styled, for example, into precise gentle waves, as may be desired. In addition, significant improvement to the smoothness of the hair surface is achieved by the application of compression and heat. It is believed the application of compression and heat, at the microscopic level, enhances of the bonding of the conditioning proteins to the surface of the hair.

After the pre-oxidizing set, an acid rinse is applied to the hair. The acid rinse works to completely remove any residue that may remain of the alkaline base hair straightening solution previously applied to the hair. In addition, the acid rinse is designed to lower the ph of the hair to within the range of about 4.5 to 5.5 ph, prior to the application of the neutralizer solution. Lowering the ph assures that the effects of any residual alkaline base hair straightening solution is eliminated. It has been found that an acid rinse having a base of citric acid works well, although other acids and combination of acids may be used. For example, malic acid, oleic acid, sorbic acid, phosphate acid, and the like, may be used. Preferably about seven eights of the solution is pure water.

The neutralizer solution is then applied to the hair and is allowed to remain on the hair for a time period sufficient to eliminate the structurally elastic condition of the hair. Typically, it takes about 10 minutes for the hair to become neutralized. It is important to avoid application of the neutralizer solution to the root of the hair. Application of the neutralizer solution to the root of the hair leads to rapid oxidation of the hair which can cause hair breakage. It is therefor highly desirable to allow the hair roots to oxidize naturally.

After the structurally elastic condition of the hair has been eliminated by the application of the neutralizer solution, the hair is rinsed with lukewarm water with low water pressure to remove the neutralizer solution and its residue.

Although at this point the hair straightening process is essentially complete, further improvement to the surface structure of the straightened hair can be accomplished when the following additional steps are followed. These last steps improve the sheen of the hair and strengthen the hair so that the effects of the process last longer and are easier to maintain.

After rinsing out the neutralizer solution, the hair is sprayed with another hair repairing solution containing less than about 2% oil. It is desirable that this solution, or hair conditioner, contains a protein base of Keratin and Collagen, although other hair protein bases may be used, if desired. It has been found that the protein combinations of Hydroxypropyltrimonium Hydrolized Keratin, Hydrolyzed Collagen, Rosin Hydrolyzed Collagen, and Hydrolyzed Elastin work well when used in combination along with glove oil and matricidal oil. It is desirable for the solution to be a clear liquid as it will remain in the hair as the hair is dried.

Once the hair repairing solution has been applied, the hair is dried until approximately 90 to 95 percent of the moisture has been removed. Preferably, this is accomplished by towel drying the hair followed with combing and blow drying.

Finally, the flat hair iron is applied to the hair in the same manner as it was in the pre-oxidizing set step. With the proteins and oil present, and with the application of compression and heat from the hair iron, further improvement of the surface structure of the hair is achieved. The conical flap layers of the hair are compressed tightly together by the iron, and with the protein and heat present the flap layers of each hair strand are bonded to produce an even smoother hair surface. This improves the sheen of the hair and strengthens the hair so that the effects of the process last longer.

Once the process is complete it is desirable to avoid shampooing the hair for 48 hours to allow the effects of the process to completely cure.

EXAMPLE 2

This example is intended for use on generally undamaged thick hair. Such hair, for example, would have very little, if any, split ends or frizzles, and already be in a generally straight condition. Typically such hair has not been previously permed or colored.

The steps in this example are identical to those in Example 1 but with the following change.

The hair repairing solution used in this example comprises a liquid protein conditioner containing proteins of just Keratin, and Collagen. Preferably, a combination of the proteins of hydroxypropyltrimonium Hydrolyzed Keratin, Isostearoyl Hydrolized Collagen, and Hydroxypropyltrimonium Collagen in a hair repairing solution for treating thick hair produces excellent results. It is believed these proteins, compared to the proteins used in the hair repairing solution of Example 1, are finer molecules which can more deeply penetrate thick hair. However the hair repairing solutions of either Example 1 or Example 2 will provide satisfactory results, and one skilled in the art will realize numerous other protein combinations are possible as well.

EXAMPLE 3

This example is intended for use on generally slightly damaged thin hair. Such hair, for example, would have a moderate amount of split ends or frizzles, or may have been previously permed or colored.

The steps in this example are identical to those in Example 1 but with an additional step and two changes discussed below.

After the initial wash and rinse, but before the hair straightening solution is applied, the hair repairing solution of Example 1 is applied to the hair. This advanced conditioning preparation introduces the conditioner proteins to the hair much earlier in the process in order to allow more time for the protein to react and bond with the slightly damaged thin hair.

The two changes in this Example as compared to Example 1 is that the iron temperature may be reduced, as desired, to approximately 160 degrees Celsius when being applied to the slightly damaged portions of the hair, and the stretch test is initially done after the alkaline solution has been in the hair between about ten to sixteen minutes. Generally, it is desirable to reduce the temperature of the iron as the damage present in the hair increases.

EXAMPLE 4

This example is intended for use on generally slightly damaged thick hair. Such hair, for example, would have a moderate amount of split ends or frizzles, or may have been previously permed or colored.

The steps in this example are identical to those in Example 2 but with an additional step and two changes as discussed below.

After the initial wash and rinse, but before the hair straightening solution is applied, the hair repairing solution of Example 2 is applied to the hair. This advanced conditioning preparation introduces the conditioner proteins to the hair much earlier in the process in order to allow more time for the protein to react and bond with the slightly damaged thick hair.

The only two changes in this Example compared to Example 2 is that the iron temperature may be reduced, as desired, to approximately 160 degrees Celsius when being applied to the slightly damaged portions of the hair, and that the stretch test is conducted between about ten to sixteen minutes after the solution has been applied to the hair.

EXAMPLE 5

This example is intended for use on generally highly damaged thin hair. Such hair, for example, would have a substantial amount of split ends or frizzles, may also have been previously permed or colored, or may have been bleached.

The steps in this example are identical to those in Example 3 but with the following changes.

After the initial wash and rinse, but before the hair straightening solution is applied, when the hair repairing solution of Example 1 is applied to the hair, an additional application of the hair repairing solution containing about up to about 5% of oil is applied to the hair. This advanced conditioning preparation not only introduces additional conditioner proteins to the hair much earlier in the process, but also introduces the oil to the hair much earlier which helps prevent further damage to the hair during the process. The oil acts as a protective barrier to prevent damage to the hair due to the action of the alkaline base hair straightening solution, and is selectively applied to the most damaged portions of the hair.

In addition, after the hair has been shampooed and rinsed to insure all of the residue of alkaline base hair straightening solution has been removed, the hair repairing solution containing up to about 5% of oil is again applied to the hair, particularly to the most damaged portions of the hair. Again, the introduction of additional protein and oil helps prevent further damage to the hair such as breakage. After the application, the hair is towel dried.

The other two changes in this Example compared to Example 3 is that the iron temperature may be reduced, as desired, from 160 degrees Celsius to approximately 130 degrees Celsius when being applied to the highly damaged portions of the hair, and the stretch test is conducted between about four to eight minutes after the alkaline solution has been applied to the hair.

EXAMPLE 6

This example is intended for use on generally highly damaged thick hair. Such hair, for example, would have a substantial amount of split ends or frizzles, may also have been previously permed or colored, or may have been bleached.

The steps in this example are identical to those in Example 4 but with the following changes.

After the initial wash and rinse, but before the hair straightening solution is applied, when the hair repairing solution of Example 2 is applied to the hair, an additional application of the hair repairing solution containing up to about 5% of oil is applied to the hair. This advanced conditioning preparation not only introduces additional conditioner proteins to the hair much earlier in the process, but also introduces the oil to the hair much earlier. The oil helps prevent the hair from drying out during the process which is very desirable, for damage and breakage of the hair can result if the hair dries out before being neutralized.

In addition, after the hair has been shampooed and rinsed to insure all of the residue of alkaline base hair straightening solution has been removed, the hair repairing solution containing up to about 5% of oil is again applied to the hair, particularly to the most damaged portions of the hair. Again, the introduction of additional protein and oil helps prevent further damage to the hair such as breakage. After the application, the hair is towel dried.

The two other changes in this Example compared to Example 4 is that the iron temperature may be reduced, as desired, from 160 degrees Celsius to approximately 130 degrees Celsius when being applied to the highly damaged portions of the hair, and the stretch test is conducted between about four to eight minutes after the alkaline solution has been applied to the hair.

What has been described are preferred embodiments in which modifications and changes may be made without departing from the spirit and scope of the accompanying claims.

Obviously many modifications and variations of the present invention are possible in light of the above teachings. It is therefore to be understood that, within the scope of the appended claims, the invention may be practiced otherwise than as specifically described.

What is claimed is:

1. An improved hair repair and straightening process comprising the steps of:
   washing and rinsing said hair;
   applying an alkaline base hair straightening solution to said hair;
   allowing said alkaline base hair straightening solution to remain on said hair until said hair transitions into a structurally elastic condition;
   suspending said hair in said structurally elastic condition by rinsing out said alkaline base hair straightening solution from said hair;
   applying a hair repairing solution to said hair;
   applying a pre-oxidizing set to said hair structure by compressing said hair under heat;
   applying an acid rinse to said hair; and
   applying a neutralizer solution to said hair for a time period sufficient to eliminate said structurally elastic condition of said hair.

2. An improved hair repair and straightening process of claim 1 comprising the additional step of covering the hair with a plastic wrap while said alkaline base hair straightening solution remains in said hair.

3. An improved hair repair and straightening process of claim 1 wherein said structurally elastic condition of said hair is established when said hair becomes able to elastically stretch approximately between about 25 to 50 percent.

4. An improved hair repair and straightening process of claim 3 further comprising the step of determining when said structurally elastic condition of said hair is established by grasping about four or more strands of hair of about three centimeters apart and pulling on said strands of hair, said structurally elastic condition established when said strands elastically stretch to approximately about four to four and a half centimeters.

5. An improved hair repair and straightening process of claim 1 wherein said alkaline based hair straightening solution has a jell-like consistency adapted to more easily be removed when rinsed from said hair.

6. An improved hair repair and straightening process of claim 1 further comprising the final steps of;
   rinsing out said neutralizer solution from said hair,
   applying a conditioner to said hair,
   blow drying said hair, and
   re-compressing said hair under heat.

7. An improved hair repair and straightening process of claim 1 wherein a hair iron is used style said hair while compressing said hair under heat during said pre-oxidizing set.

8. An improved hair repair and straightening process of claim 1 wherein oil is present in said hair repairing solution.

9. An improved hair repair and straightening process of claim 1 wherein said step of suspending said hair in said structurally elastic condition further comprises:
   shampooing said hair;
   rinsing said hair; and
   re-applying said hair repairing solution.

10. An improved hair repair and straightening process of claim 1 further comprising the step of:
    applying said hair repairing solution to said hair prior to applying said alkaline base hair straightening solution to said hair.

11. An improved hair repair and straightening process comprising the steps of:
    washing and rinsing said hair;
    applying a thioglycolic alkaline base hair straightening solution to said hair except to the nape section of said hair, said alkaline base hair straightening solution having a jell-like consistency;
    covering said hair with a plastic wrap while said alkaline base hair straightening solution remains in said hair;
    allowing said alkaline base hair straightening solution to remain on said hair until said hair transitions into a structurally elastic condition, said structurally elastic condition established when said hair elastically stretches approximately between about 25 to 50 percent;
    determining when said hair transitions into said structurally elastic condition by grasping about four or more strands of hair of about three centimeters apart and pulling on said strands of hair, said structurally elastic condition established when said strands elastically stretch to approximately about four to four and a half centimeters;
    noting the time duration in which said alkaline base hair straightening solution has remained in said hair up to the establishment of said structurally elastic condition;
    removing said plastic wrap and applying said alkaline base hair straightening solution to said hair in said nape section
    re-placing said plastic wrap and allowing said alkaline base hair straightening solution to remain on said hair approximately one half the time of said time duration;

suspending said hair in said structurally elastic condition by removing said plastic wrap and rinsing out said alkaline base hair straightening solution from said hair;

applying a hair repairing solution containing protein molecules to said hair;

applying a pre-oxidizing set to said hair structure by compressing said hair axially under heat with a flat hair iron to style said hair and substantially improve the surface structure of said hair by promoting bonding of said protein molecules to said hair;

applying an acid rinse to said hair to remove any residual effects of said alkaline hair straightening solution; and applying a neutralizer solution to said hair for a time period sufficient to eliminate said structurally elastic condition of said hair.

* * * * *